United States Patent [19]

Ohsaki et al.

[11] Patent Number: 5,783,717
[45] Date of Patent: Jul. 21, 1998

[54] METHOD FOR PURIFYING ORGANOMETAL COMPOUND

[75] Inventors: Hiromi Ohsaki; Toshinobu Ishihara; Kazuyuki Asakura; Isao Kaneko; Kouhei Satou, all of Niigata, Japan

[73] Assignee: Shin-Etsu Chemical Co., Ltd., Tokyo, Japan

[21] Appl. No.: 517,093

[22] Filed: Aug. 21, 1995

[30] Foreign Application Priority Data

Aug. 19, 1994 [JP] Japan ................. 6-195470

[51] Int. Cl.$^6$ ................. C07F 5/06; C07F 3/00
[52] U.S. Cl. ................. 556/187; 556/1; 556/70; 556/121; 556/170; 556/190
[58] Field of Search ................. 556/170, 187, 556/190, 1, 121, 70

[56] References Cited

U.S. PATENT DOCUMENTS

| | | | |
|---|---|---|---|
| 4,797,500 | 1/1989 | Kadokura et al. | 556/1 |
| 4,847,399 | 7/1989 | Hallock et al. | 556/1 |
| 5,288,885 | 2/1994 | Smit et al. | 556/1 |

FOREIGN PATENT DOCUMENTS 2201418  9/1988  United Kingdom.

*Primary Examiner*—Porfirio Nazario-Gonzalez
*Attorney, Agent, or Firm*—Sughrue, Mion, Zinn, Macpeak & Seas, PLLC

[57] ABSTRACT

A method for purifying an organometal compound by removing oxygen atom-containing compounds included in the organometal compound as impurities is herein disclosed. The method comprises the steps of mixing an organometal compound represented by the following formula:

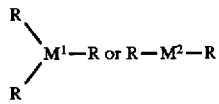

with a crude product including an oxygen atom-containing compound represented by the following formula: $R_{3-n} M^1(OR)_n$ or $R_{2-m} M^2(OR)_m$ and an alkylaluminum chloride represented by the formula: $X_{6-q}Al_2R$ and then distilling the resulting mixture. In the foregoing formulas, R's may be the same or different and each represents an alkyl group having 1 to 3 carbon atoms; $M^1$ represents a trivalent metal element; $M^2$ represents a divalent metal element; n is an integer of 1, 2 or 3; m is an integer of 1 or 2; q is an integer ranging from 1 to 5; and X represents a chlorine atom.

3 Claims, 1 Drawing Sheet

METHOD FOR PURIFYING ORGANOMETAL COMPOUND

BACKGROUND OF THE INVENTION

The present invention relates to a method for purifying an organometal compound by removing oxygen atom-containing compounds included in the organometal compound which is useful in MOCVD (metal organic chemical vapor deposition) method for preparing a compound semiconductor as a material for the epitaxial growth of the compound semiconductor.

Recently, III–V and II–VI compound semiconductors have widely been used in the fields of, for instance, semiconductor light emitting elements and microwave transistors and have gradually been used in IC's for high speed computers and IC's for optoelectronics while making use of the excellent characteristic properties of the compound semiconductors. Such compound semiconductors are produced by epitaxially growing the crystals of organometal compounds according to, for instance, the MOCVD method.

The MOCVD method is one of the crystal growth methods which have widely been used for forming epitaxial thin films of compound semiconductors or mixed crystal semiconductors. This method comprises pyrolyzing organometal compounds such as trimethylaluminum, trimethylgallium and dimethylzinc as raw materials to grow thin films of crystals thereof.

The quality of a compound semiconductor obtained through the epitaxial growth of an organometal compound is greatly affected by the purity of the organometal compound as a raw material. This is because the oxygen atoms included in the organometal compound have an extremely bad influence on the electrical and optical properties of the resulting compound semiconductor.

Journal of Crystal Growth, 157 (1984) discloses that the presence of oxygen atoms in an epitaxially grown thin film leads to substantial reduction in characteristic properties of the thin film, i.e., the semiconductor. This is because oxygen atoms react with an organometal compound as a raw material for the epitaxially grown thin film to form an oxygen atom-containing compound and the latter in turn impairs the characteristic properties of the thin film or semiconductor.

Organometal compounds include, for instance, trimethylaluminum, triethylalminum, trimethylgallium, dimethylzinc and diethylzinc, with trimethylaluminum being particularly susceptible to take in oxygen atoms. Dimethyl momomethoxyaluminum formed through the reaction of trimethylaluminum with oxygen serves as an impurity and accordingly results in the reduction in the characteristic properties of the semiconductor. For this reason, there has been employed a method for reducing, in particular, the content of dimethyl momomethoxyaluminum present in trimethylaluminum.

Applied Organometallic Chemistry, 5,319 (1991) discloses a method for purifying an organometal compound which comprises the step of distilling a crude product of the organometal compound including an oxygen atom-containing compound as an impurity, in the presence of an aluminum trihalide. In addition, Japanese Patent Application Publication No. 5-29371 discloses a method comprising adding a reducing agent such as a metal hydride compound.

In the method comprising distilling the crude product in the presence of an aluminum trihalide, however, the aluminum trihalide to be added is quite susceptible to oxidation and therefore, it is difficult to purify the aluminum trihalide once oxidized. Accordingly, if the crude product is purified using an aluminum trihalide, the resulting purified product has an oxygen concentration of not less than 50 ppm.

On the other hand, the method which comprises adding a metal hydride compound requires a high production cost since the metal hydride compound is highly expensive and therefore, the method is unsuitable from the industrial standpoint. Moreover, if the metal constituting the metal hydride compound to be added differs from that present in the organometal compound to be purified, the metal hydride compound remains in the organometal compound to be purified as an impurity.

SUMMARY OF THE INVENTION

The present invention has been developed to solve the foregoing problems associated with the conventional techniques and accordingly, it is an object of the present invention to provide a method for purifying an organometal compound by removing an oxygen atom-containing compound included therein.

According to the present invention, the foregoing object can effectively be accomplished by providing a method for purifying an organometal compound which comprises the steps of mixing an organometal compound represented by the following formula:

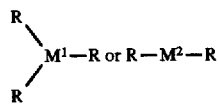

with a crude product including an oxygen atom-containing compound represented by the following formula: $R_{3-n}M^1(OR)_n$ or $R_{2-m}M^2(OR)_m$ and an alkylaluminum chloride represented by the formula: $X_{6-q}Al_2R_q$ and then distilling the resulting mixture. In the foregoing formulas, R's may be the same or different and each represents an alkyl group having 1 to 3 carbon atoms; $M^1$ represents a trivalent metal element; $M^2$ represents a divalent metal element; n is an integer of 1, 2 or 3; m is an integer of 1 or 2; q is an integer ranging from 1 to 5; and X represents a chlorine atom. The method for purifying an organometal compound according to the present invention more specifically comprises the following steps. First, a crude product of an organometal compound is introduced into a glass or stainless steel container equipped with a distillation column. Then an alkylaluminum chloride is added to the container and the content thereof is heated to remove any oxygen atom-containing compound included in the organometal compound. In this respect, the content of the container is not particularly stirred. The alkylaluminum chloride is desirably added to the crude product in an amount ranging from 0.1 to 20 parts by weight per 100 parts by weight of the latter. This is because if the amount thereof is less than 0.1 part by weight, the organometal compound is not satisfactorily purified, while any further improvement in the effect of the addition of the alkylaluminum chloride is not expected even if it is used in an amount greater than 20 parts by weight. The alkylaluminum chloride is at least one member selected from the group consisting of methylaluminum sesquichloride, ethylaluminum sesquichloride, diethylaluminum chloride, ethylaluminum dichloride and dimethylaluminum chloride.

The purified organometal compound is represented by the following formula:

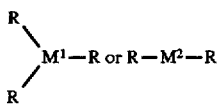

and the oxygen content thereof is not more than 50 ppm. In the formula, R, $M^1$ and $M^2$ are the same as those defined above. The organometal compound may be, for instance, trimethylaluminum.

DETAILED EXPLANATION OF THE INVENTION

Figure 1:
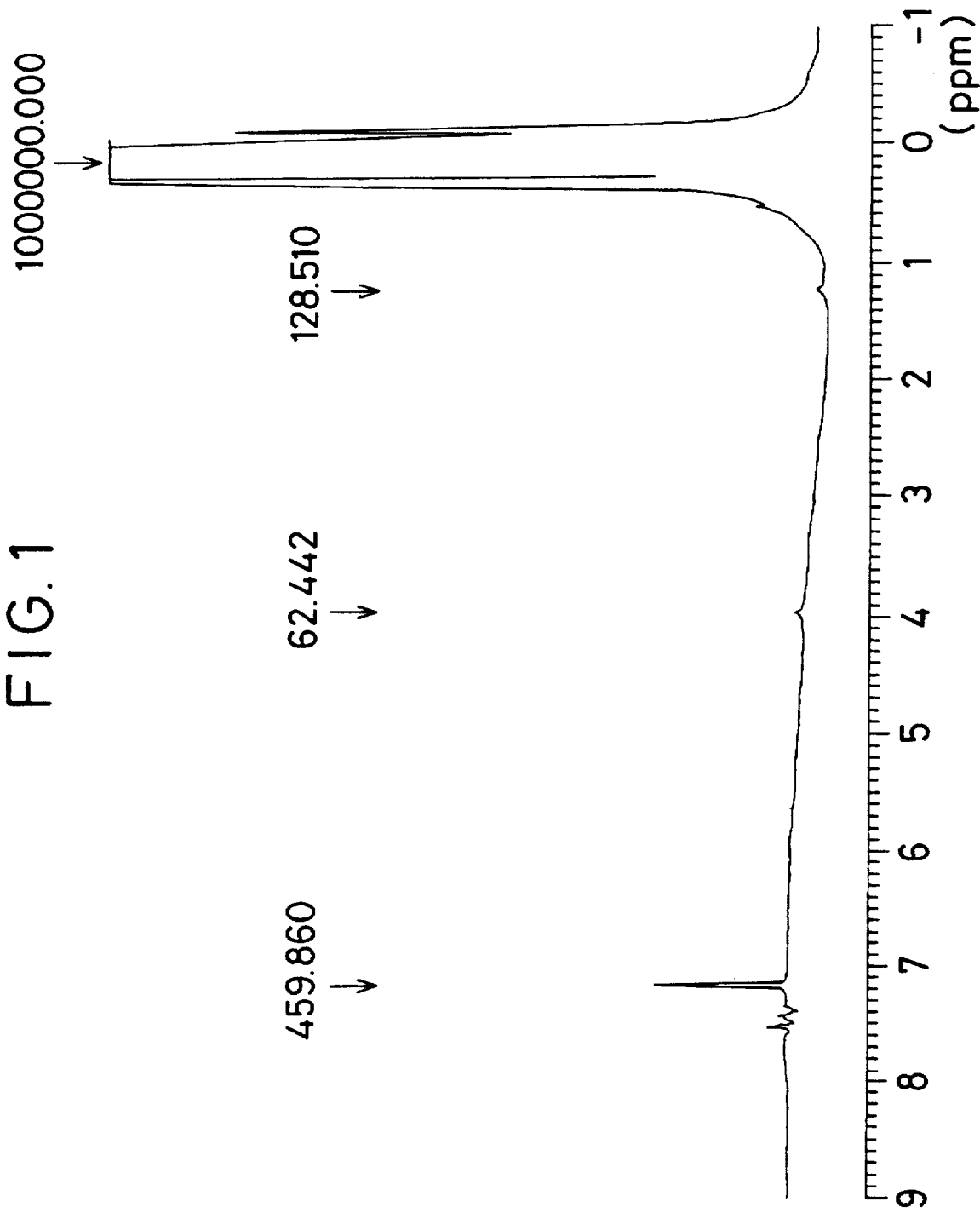
FIG. 1 is a diagram showing the NMR spectrogram, the integral curve and the integrated intensity of a crude product comprising trimethylaluminum and oxygen atom-containing compounds included therein as impurities.

The alkylaluminum chloride is not so susceptible to surface oxidation as compared with, for instance, aluminum trihalides. Therefore, if a crude product which comprises an organometal compound and oxygen atom-containing compounds as impurities is mixed with an alkylaluminum chloride and then the resulting mixture is distilled, any possibility of forming new oxygen atom-containing compounds is reduced. For this reason, the method of the present invention permits the production of an organometal compound having a high purity.

Embodiments of the present invention will hereinafter be described in more detail, but the present invention is not restricted to these specific embodiments.

The method for purifying an organometal compound according to the present invention comprises the following steps. A crude product which comprises an organometal compound and oxygen atom-containing compounds included therein as impurities is introduced into a container equipped with a distillation column. The container is made of glass or stainless steel. After mixing the crude product with an alkylaluminum chloride, the mixture is subjected to distillation to purify the organometal compound.

The extent of the purification can be evaluated by calculating the oxygen concentrations through the measurement of the nuclear magnetic resonance (hereunder referred to as "NMR") spectrograms of the crude product and the purified product to determine the oxygen concentrations thereof and then comparing these two oxygen concentrations.

For instance, if measuring the NMR spectrograms of a crude product which comprises trimethylaluminum: $(CH_3)_3Al$ and dimethyl monomethoxyaluminum: $(CH_3)_2Al(OCH_3)$ present therein as an impurity and the purified product thereof, the oxygen concentration can theoretically be represented by the following relation:

Oxygen Concn.=(Amount of Oxygen Atoms)/(Amount of Trimethylaluminum+Amount of Dimethyl Monomethoxyaluminum)

In the NMR spectrogram, the peak area assigned to —$CH_3$ groups is regarded as A, while that ascribed to —$OCH_3$ groups is regarded as B. Since the molecular weight of trimethylaluminum is 72, that of dimethyl monomethoxyaluminum is 88 and the atomic weight of oxygen is 16, the following relations can be obtained:

Amount of Trimethylaluminum=72×(A−6/3×B)/9;

Amount of Dimethyl Monomethoxyaluminum=88×B/3;

and

Amount of Oxygen=16×B/3

The oxygen concentration in the organometal compound is determined by calculating the amounts of trimethylaluminum, dimethyl monomethoxyaluminum and oxygen according to the foregoing relations, respectively and then substituting these amounts into the following equation:

Oxygen Concn.=(Amount of Oxygen)/(Amount of Trimethylaluminum+Amount of Dimethyl Monomethoxyaluminum)

Then the degree of purification is confirmed by measuring the NMR spectrograms of the crude product and the purified product thereof to thus determine the oxygen concentrations of these products and comparing the oxygen concentration of the crude product with that of the purified product.

EXAMPLE 1

To a 1000 ml volume glass flask equipped with a glass distillation column having an outer diameter of 25 mm and a length of 300 mm, there was added 20 g of methylaluminum sesquichloride (available from Aldrich Chemical Company) without bringing the sesquichloride into contact with the air. Then 400 g of a crude product of trimethylaluminum having an oxygen content of 150 pp. was added to and mixed with the sesquichloride and the mixture was distilled with heating. Thus, 375 g of a purified product was obtained at a running point of 126° C.

The degree of purification is evaluated by measuring the NMR spectrograms of the crude product and the purified product to determine the oxygen concentration thereof and then comparing the oxygen concentration of the former to that of the latter. The NMR spectrogram of the crude product is specifically measured by the method detailed below.

A container including a crude product of trimethylaluminum which contains oxygen atom-containing compounds as impurities is fitted to the upper portion of a glass tube having an outer diameter of 8 mm. In this respect, the crude product was introduced into the glass tube after evacuating the glass tube to a pressure of $5 \times 10^{-4}$ torr. After filling the glass tube with the crude product, the product was cooled with liquid nitrogen and the glass tube was sealed using a gas burner. The sealed glass tube was accommodated in another glass test tube having an inner diameter of 9 mm to form a double tube.

The NMR spectrogram of the crude product contained in the double tube was determined using an NMR spectrometer (GSX-270 available from JEOL Ltd.). FIG. 1 is a diagram showing the NMR spectrogram, the integral curve and the integrated intensity of the crude product. The NMR spectrum of pure trimethylaluminum was detected at 0.1 ppm and that of dimethyl monomethoxyaluminum as an impurity was detected at 3.89 ppm. The oxygen concentration was calculated on the basis of the resulting integrated intensity and found to be 151 ppm.

The NMR spectrogram of the purified product is determined by the same method used above. As a result, the oxygen concentration was found to be 48 ppm.

EXAMPLE 2

The distillation and the determination of oxygen concentration was carried out by repeating the same procedures used in Example 1 except that the added amount of methylaluminum sesquichloride was changed to 10 g. As a result, the oxygen concentration of the purified product thus obtained was found to be 42 ppm.

EXAMPLE 3

The distillation and the determination of oxygen concentration was carried out by repeating the same procedures used in Example 1 except that ethylaluminum sesquichloride was substituted for the ethylaluminum sesquichloride used in Example 1. As a result, the oxygen concentration of the purified product thus obtained was found to be 45 ppm.

EXAMPLE 4

The distillation and the determination of oxygen concentration was carried out by repeating the same procedures used in Example 1 except that a crude product of trimethylgallium containing oxygen atom-containing compounds as impurities is substituted for the crude product of trimethylaluminum containing oxygen atom-containing compounds as impurities used in Example 1. As a result, the oxygen concentration of the purified product thus obtained was found to be 29 ppm.

COMPARATIVE EXAMPLE 1

The distillation and the determination of oxygen concentration was carried out by repeating the same procedures used in Example 1 except that trichloroaluminum was substituted for the methylaluminum sesquichloride used in Example 1. As a result, 368 g of a distillate was obtained and the oxygen concentration of the distillate exceeded 50 ppm and was found to be 98 ppm.

COMPARATIVE EXAMPLE 2

The distillation and the determination of oxygen concentration was carried out by repeating the same procedures used in Example 1 except that lithium aluminum hydride was substituted for the methylaluminum sesquichloride used in Example 1. As a result, a distillate was obtained and the oxygen concentration thereof exceeded 50 ppm and was found to be 110 ppm.

The method for purifying an organometal compound according to the present invention permits the reduction in the oxygen concentration of a crude product which comprises an organometal compound and oxygen atom-containing compounds as impurities to a level of not more than 50 ppm. If highly pure organometal compounds thus obtained according to the method of this invention are used in the epitaxial growth of semiconductor crystals, semiconductors of high quality can be prepared.

What is claimed is:

1. A method for purifying an organometal compound comprising the steps of mixing an organometal compound represented by the following formula:

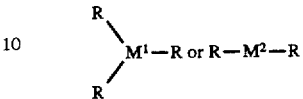

wherein R's may be the same or different and each represents an alkyl group having 1 to 3 carbon atoms; $M^1$ represents a trivalent metal element; and $M^2$ represents a divalent metal element with crude product including an oxygen atom-containing compound represented by the following formula:

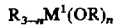

wherein n is an integer of 1, 2 or 3 or

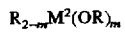

wherein m is an integer of 1 or 2 as an impurity, and an alkylaluminum chloride represented by the formula:

wherein R is the same as that defined above, q is an integer ranging from 1 to 5; and X represents a chlorine atom, and then distilling the resulting mixture.

2. The method for purifying an organometal compound according to claim 1 wherein the alkylaluminum chloride is added in an amount ranging from 0.1 to 20 parts by weight per 100 parts by weight of the crude product.

3. The method for purifying an organometal compound according to claim 1 or 2 wherein the alkylaluminum chloride is at least one member selected from the group consisting of methylaluminum sesquichloride, ethylaluminum sesquichloride, diethylaluminum chloride, ethylaluminum dichloride and dimethylaluminum chloride.

* * * * *